United States Patent [19]

Jessel, Jr. et al.

[11] Plant 4,052

[45] May 10, 1977

[54] CHRYSANTHEMUM PLANT

[75] Inventors: Walter H. Jessel, Jr., Doylestown; William E. Duffett, Akron, both of Ohio

[73] Assignee: Yoder Brothers, Inc., Barberton, Ohio

[21] Appl. No.: 677,410

[22] Filed: Apr. 15, 1976

[51] Int. Cl.[2] ..... A01H 5/00

[52] U.S. Cl. ..... Plt./82

[58] Field of Search ..... Plt./82

*Primary Examiner*—Robert E. Bagwill

*Attorney, Agent, or Firm*—Donald D. Jeffery

EXEMPLARY CLAIM

1. A new and distinct cultivar of chrysanthemum known by the cultivar name Redcoat and characterized particularly as to uniqueness by the combined characteristics of flat inflorescence form, decorative inflorescence type, red-bronze inflorescence color with minimal color oxidation; diameter across face of inflorescence up to 3.5 inches; permanence of inflorescence ranging from 14 to 21 days; tall plant height; semi-upright branching pattern; good tolerance of inflorescence to frost damage; average natural season flowering date of September 26, and average flowering response period of 7 weeks in photoperiodic controlled flowering programs.

3 Drawing Figures

The present invention comprises a new and distinct cultivar of *Chrysanthemum morifolium*, Ramat., hereinafter referred by the cultivar name Redcoat (No. 74035001).

Redcoat is a product of a planned breeding program which had the objective of creating cultivars with decorative inflorescence type, short height, spreading branching pattern, durable inflorescence, short (6 to 7 week) flowering response period, and intense red and red-bronze inflorescence color with minimal color oxidation under outdoor natural season conditions.

Redcoat was originated from a cross made in a controlled breeding program in Barberton, Ohio in the year 1973. The male, or pollen parent, was No. 73253001 (unnamed seedling), a red decorative originated by the present inventors from a cross between No. 72054013 (unnamed seedling) and No. 72032M01 (unnamed seedling). The female, or seed parent, of Redcoat was Ringoes (No. 21740E46; unpatented; commercially available), a red decorative of parentage unknown to the present invention. No. 72054013 and No. 72032M01 were products of the breeding program of the present inventors.

Redcoat was discovered and selected as a flowering plant within the progeny of the stated cross by Walter H. Jessel, Jr. on May 4, 1974 in an outdoor field in Ft. Myers, Fla.

The first act of asexual reproduction of Redcoat was accomplished when vegetative cuttings were taken from the initial selection in July, 1974 in a controlled environment in Barberton, Ohio by a technician working under formulations established and supervised by William E. Duffett and Walter H. Jessel, Jr. Horticultural examination of selected units initiated October 10, 1974 has demonstrated that the combination of characteristics as herein disclosed for Redcoat are firmly fixed and are retained through successive generations of asexual reproduction.

Redcoat has not been observed under all possible environmental conditions. The phenotype may vary significantly with variations in environment such as temperature, light intensity, and daylength. The following observations, measurements, and comparisons describe plants grown in a field in Barberton, Ohio under conditions which are generally described in *Local Climatological Data, Annual Summary with Comparative Data, Akron, Ohio*, U.S. Department of Commerce, National Oceanic and Atmospheric Administration, Environmental Data Service, Washington, D.C. 1973, 1974, 1975, and *Tables of Sunrise, Sunset, and Twilight*. Supplement to the American Emphemeris, 1946., U.S. Naval Observatory, Washington, D.C., pg. 103.

The following traits have been repeatedly observed and are determined to be basic characteristics of Redcoat which in combination distinguish this chrysanthemum as a new and distinct cultivar:

1. Flat inflorescence form.
2. Decorative inflorescence type.
3. Red-bronze inflorescence color with minimal color oxidation.
4. Diameter across face of inflorescence up to 3.5 inches.
5. Permanence of inflorescence ranging from 14 to 21 days.
6. Tall plant height (requiring 1–2 long day weeks prior to short days and 1 application of 2500 ppm B9-SP to attain a flowered plant height of 12 to 15 inches).
7. Semi-upright branching pattern.
8. Good tolerance of inflorescence to front damage.
9. Average natural season flowering data of September 26.
10. Average flowering response period of 7 weeks in photoperiodic controlled flowering programs.

The accompanying photographic drawings show typical inflorescence and foliage characteristics of Redcoat. It is noted that difficulty was encountered in obtaining photographs accurately representing the true inflorescence color of Redcoat. The color readings in the following description are, however, correct. Sheet 1 is a color photograph of Redcoat. Sheet 2 is a black and white photograph showing three views of the inflorescence of Redcoat. Sheet 3 is a black and white photograph showing the foliage of Redcoat at three stages of growth.

Of the many commercially available cultivars known to the present inventors, the most similar existing cultivars in comparison to Redcoat are Ruby Mound (No. 21600E01; unpatented) and Scarleteer (No. 64031002; unpatented). Reference is made to attached

CHART A

COMPARISON OF REDCOAT, RUBY MOUND AND SCARLETEER

| CULTIVAR | INFLORESCENCE COLOR | INFLORESCENCE FORM AND TYPE | AVERAGE NATURAL SEASON FLOWER DATE | PLANT HEIGHT | FROST TOLERANCE | BRANCHING PATTERN |
|---|---|---|---|---|---|---|
| Redcoat | Red-Bronze | Flat Decorative | September 26 | Tall, from 14 to 15 inches | Good | Semi-upright |
| Ruby Mound | Red-blue | Flat Decorative | September 15 | Short, from 9 to 10 inches | Poor | Semi-spreading |
| Scarleteer | Red-orange | Flat Decorative | October 2 | Tall, from 14 to 15 inches | Medium | Semi-spreading |

COMPARISONS MADE OF PLANTS GROWN UNDER NATURAL SEASON OUTDOOR FIELD CONDITIONS IN BARBERTON, OHIO

Chart A which compares certain characteristics of Redcoat with the same characteristics of the above identified cultivars. General comparisons are as follow:

1. In comparison to Ruby Mound, Redcoat has different inflorescence color with less color oxidation, later natural season flower date, taller plant height, better tolerance of frost, and more upright branching pattern. The inflorescence form and inflorescence type of Redcoat are similar to those of Ruby Mound.

2. In comparison to Scarleteer, Redcoat has different inflorescence color, earlier natural season flower date, better tolerance of frost, and more upright branching pattern. The inflorescence form, inflorescence type, and plant height of Redcoat are similar to those of Scarleteer.

In the following description, color references are made to The Munsell Limit Color Cascade, 1972 edition. The color values were determined between 11:00 and 11:30 A.M. on Oct. 14, 1975 under 120 foot-candle light intensity at Barberton, Ohio.

Botanical Classification: *Chrysanthemum morifolium, Ramat.*, cv Redcoat.

INFLORESCENCE

Capitulum:

*Form.*—Flat.
*Type.*—Decorative.
*Permanence.*—14–21 days.
*Diameter across face.*—3.0 to 3.5 inches.

Corolla of ray floret:

*Texture (adaxial).*—Glabrous.
*Appearance and form.*—Ligulate.
*Arrangement.*—Whorled on receptacle.
*Persistence.*—Resists shatter.
*Color (abaxial).*—29-4 to 37-15.
*Color (adaxial).*—29-2 to 31-3 streaked with 31-3.

Reproductive organs:

*Androecium.*—Present disc florets; scant pollen.
*Gynoecium.*—Present both ray and disc florets.

PLANT

General apperance: semi-upright; tall height.
Duration and Texture: herbaceous; perennial.
Foliage:

*Color (abaxial).*—Between 22-13 and 22-14.
*Color (adaxial).*—22-12 overcast with white.
*Shape.*—Spatulate; deeply lobed.
*Texture.*—Glabrous.
*Arrangement.*—Alternate.
*Venation.*—Prominent.
*Margin.*—Moderately serrated.

We claim:

1. A new and distinct cultivar of chrystanthemum known by the cultivar name Redcoat and characterized particularly as to uniqueness by the combined characteristics of flat inflorescence form, decorative inflorescence type, red-bronze inflorescence color with minimal color oxidation; diameter across face of inflorescence up to 3.5 inches; permanence of inflorescence ranging from 14 to 21 days; tall plant height; semi-upright branching pattern; good tolerance of inflorescence to frost damage; average natural season flowering date of September 26, and average flowering response period of 7 weeks in photoperiodic controlled flowering programs.

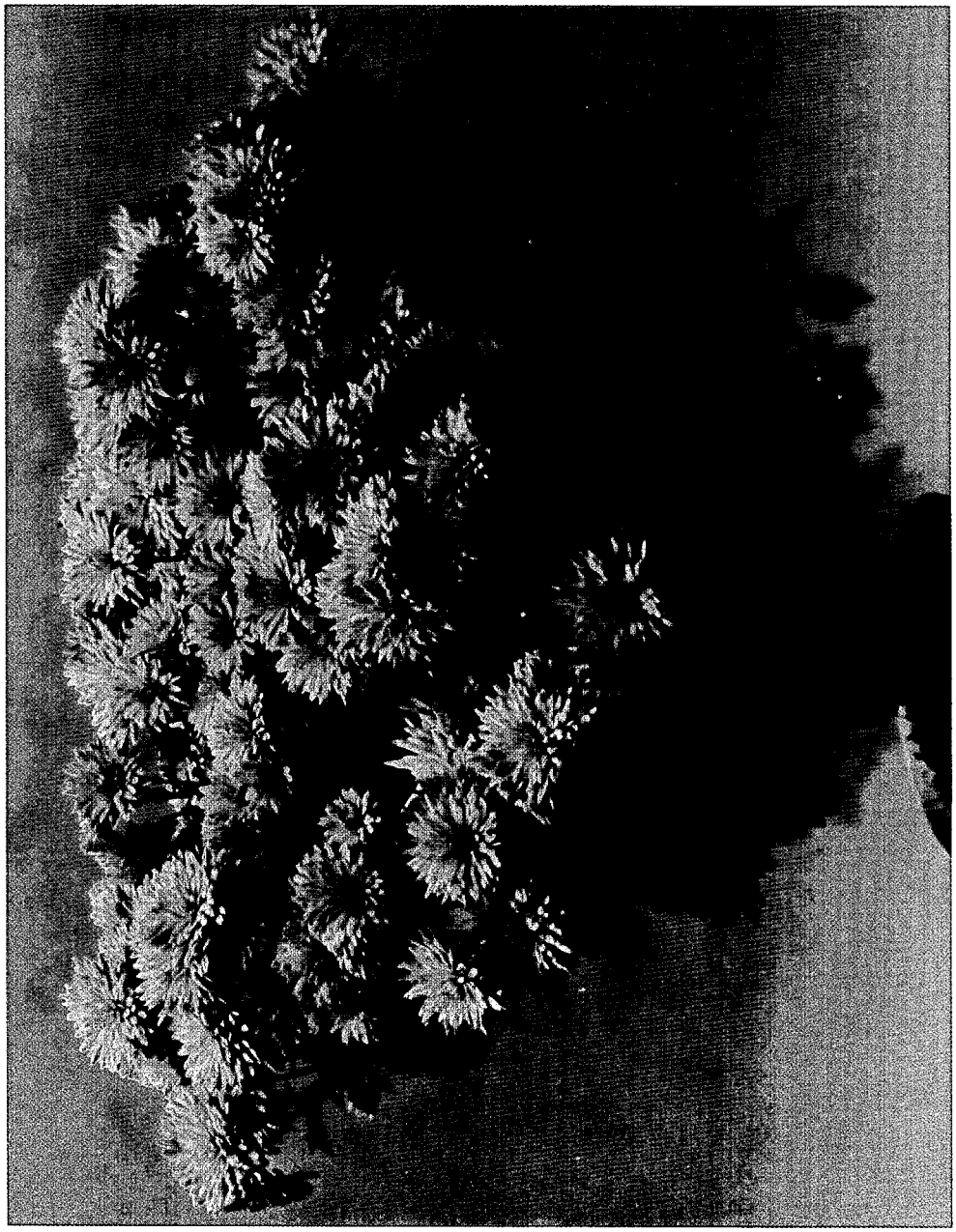

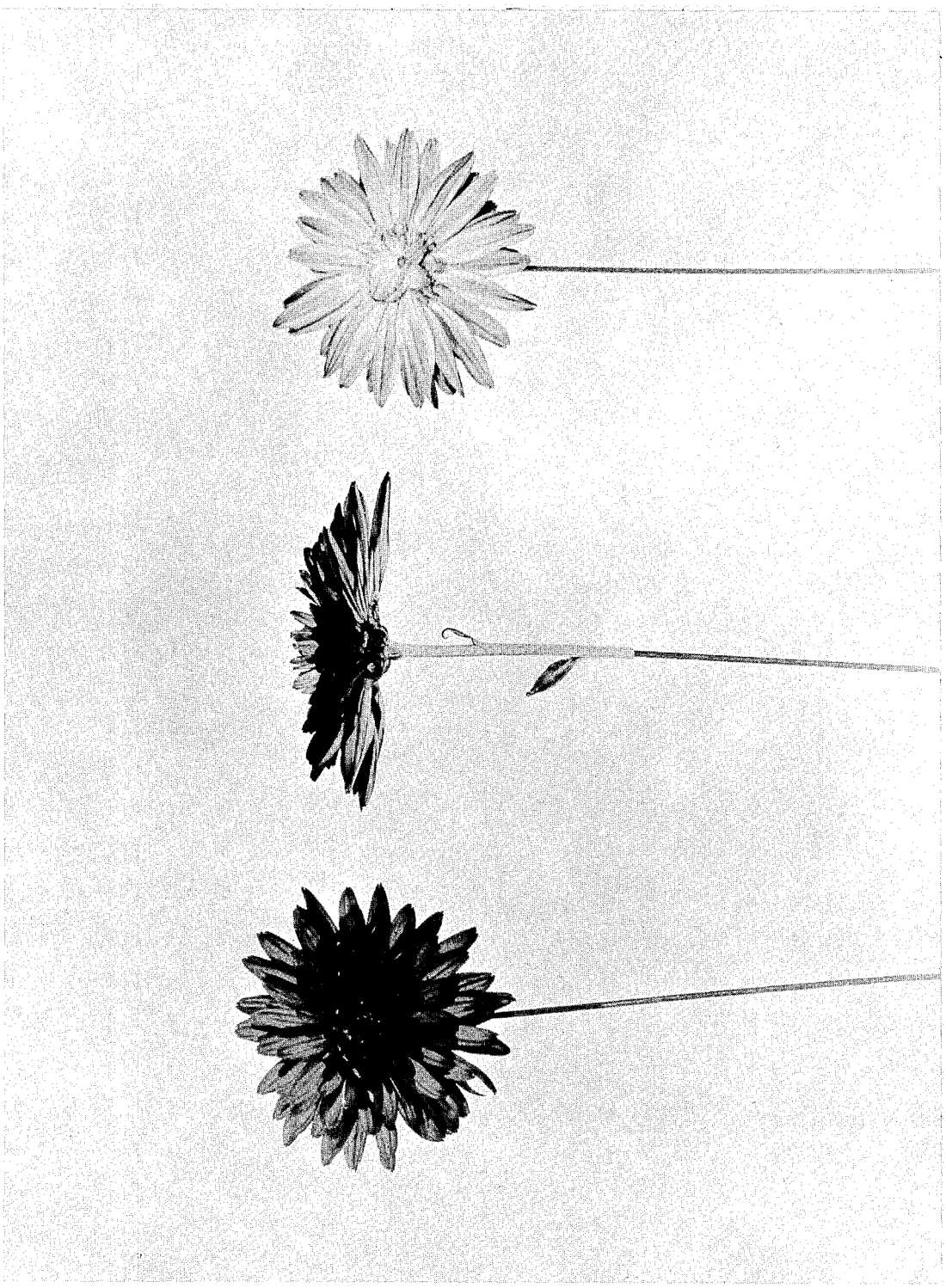

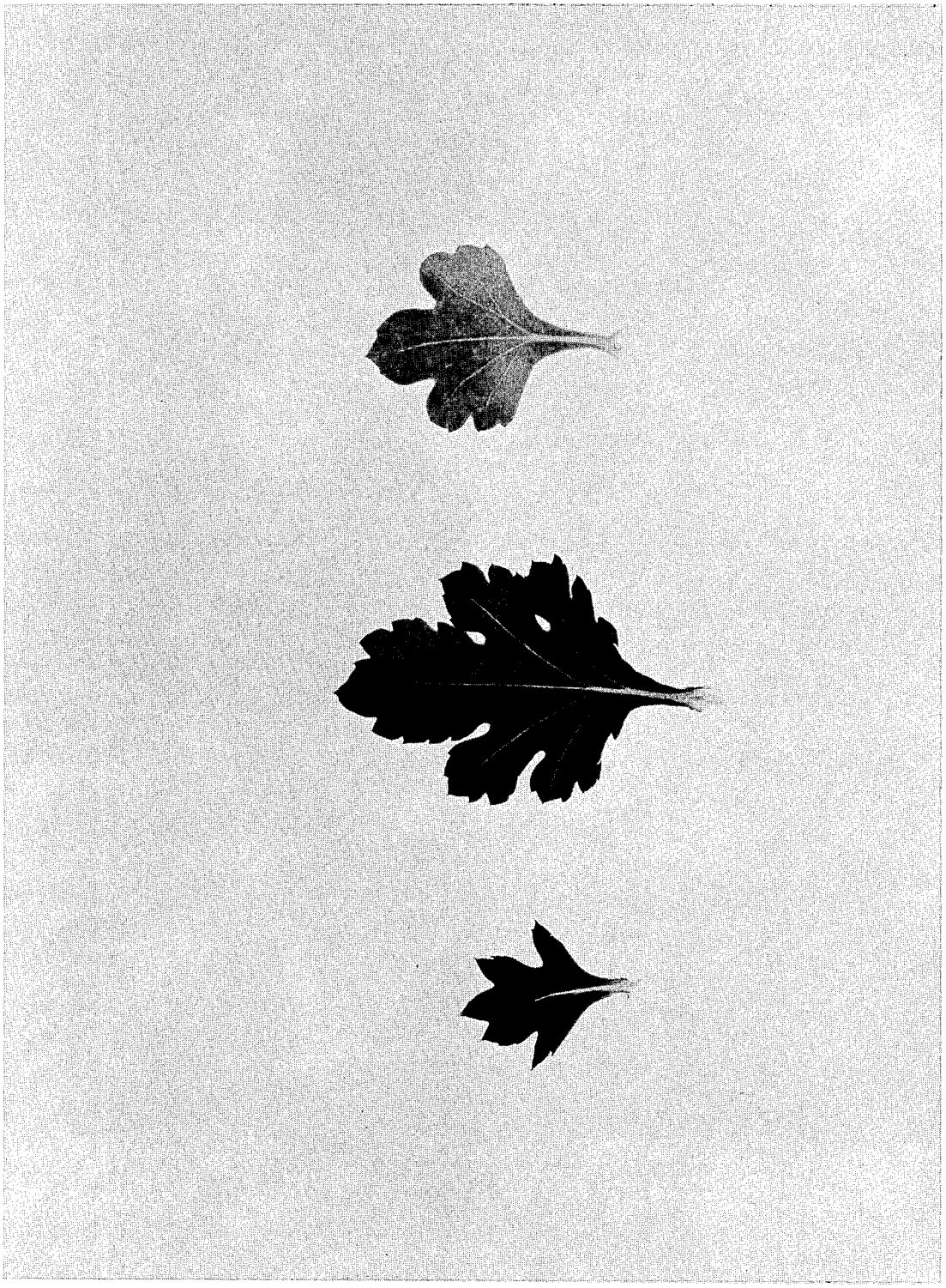

* * * * *